US00PP19524P2

(12) United States Plant Patent
Kordes

(10) Patent No.: US PP19,524 P2
(45) Date of Patent: Dec. 2, 2008

(54) HYBRID TEA ROSE PLANT NAMED 'KORMIXOSIA'

(50) Latin Name: *Rosa hybrida*
Varietal Denomination: KORmixosia

(75) Inventor: Tim-Hermann Kordes, Offenseth-Sparrieshoop (DE)

(73) Assignee: W. Kordes Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 11/725,645

(22) Filed: Mar. 19, 2007

(51) Int. Cl.
*A01H 5/00* (2006.01)

(52) U.S. Cl. ..... Plt./133

(58) Field of Classification Search ..... Plt./133
See application file for complete search history.

*Primary Examiner*—Annette H Para
*Assistant Examiner*—S. B. McCormick-Ewoldt

(57) ABSTRACT

A new and distinct variety of rose with long lasting, novel pink flowers, and attractive foliage with good disease resistance. It exhibits uniform upright growth with abundant flowers. The new variety propagates well by grafting. This new and distinct variety has shown to be uniform and stable in the resulting generations from asexual propagation.

1 Drawing Sheet

CROSS REFERENCES AND FEDERAL R&D STATEMENT

There are no cross referenced or related applications. This variety was developed without the aid of any research grant.

Latin name of genus and species: The botanical classification of the new rose plant is *Rosa hybrida.*

Variety denomination: The denomination of the new variety is 'KORmixosia'.

BACKGROUND OF THE INVENTION

The new variety of rose plant of the present invention originated from a controlled crossing in a breeding program of two distinct parents during the summer of 1999. The parents utilized in the hybridization were 'Osiana', a patented rose with U.S. Plant Pat. No. 7,660 filed on May 31, 1990; and an un-named seedling created by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORmixosia'.

SUMMARY OF THE INVENTION

The new rose plant may be distinguished from its seed parent, 'Osiana', by the following combination of characteristics:

1. 'KORmixosia' has cream-apricot blooms with a long, high centered bud while 'Osiana' has champagne colored blooms with a rounded bud; and
2. 'KORmixosia' has flowers with moderate fragrance while 'Osiana' has little to no fragrance.

The new rose plant may be distinguished from its pollen parent, an un-named seedling, by the following combination of characteristics:

1. 'KORmixosia' has cream-apricot, very double flowers while the un-named seedling has dark pink, double flowers; and
2. 'KORmixosia' has flowers with moderate fragrance while the un-named seedling has a strong fragrance.

The objective of the hybridization was to create a new and distinct rose plant with unique qualities, such as:

1. Uniform growth and flowering;
2. Abundant attractive, recurrent, and fragrant flowers;
3. Attractive and abundant foliage; and
3. Resistance to diseases encountered in landscapes and gardens.

This combination of qualities is not present in prior rose cultivars. These objectives have been substantially achieved and in that distinguish 'KORmixosia' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORmixosia' was selected in May, 2000 from the seedling beds to be asexually propagated for further evaluation. The first asexual propagation of 'KORmixosia' was done by budding to seedling understocks in July, 2000 at the W. Kordes Söhne Nursery in Offenseth-Sparrieshoop, Germany.

This initial and other subsequent propagations conducted in controlled environments show that the foregoing and all other characteristics of 'KORmixosia' come true to form and are transmitted through succeeding generations.

BRIEF DESCRIPTION OF THE DRAWING

The accompanying color illustration shows as true as is reasonably possible to obtain in color photographs of this type, the typical characteristics of the foliage, flower buds, and flowers of 'KORmixosia'.

DETAILED BOTANICAL DESCRIPTION

The following is a description of 'KORmixosia', as observed growing in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORaburg', a rose variety from the same inventor described and illustrated in U.S. Plant Pat. No. 17,763 applied for on Mar. 2, 2005 are compared to 'KORmixosia' in Chart 1.

CHART 1

| Characteristic | 'KORmixosia' | 'KORaburg' |
|---|---|---|
| Pistils. | Approx. 35-40 present. | Approx. 120 present. |
| Petal count. | 70-80 petals. | 25-30 petals. |
| Leaf size. | Approx. 135-140 mm (l) × 115-125 mm (w). | Approx. 160 mm (l) × 120 mm (w). |

Parents:

*Seed parent.*—'Osiana'.

*Pollen parent.*—Un-named seedling.

Classification:

*Botanical classification.*—*Rosa hybrida*, 'KORmixosia'.

*Commercial classification.*—Hybrid Tea rose.

FLOWER AND FLOWER BUD

Blooming habit: Recurrent.

Flower bud:

*Size.*—Upon opening, 45–55 mm in length from base of receptacle to end of bud. The diameter of the bud is 30–35 mm.

*Bud form.*—Long. Pointed ovoid. High centered.

*Bud color.*—As sepals first unfold, bud color is Red-Purple Group 63C with intonations of Red-Purple Group 63B. When ¼ open, the upper surface of petals is Red-Purple Group 63D, and the lower surface is Red-Purple Group 63C with limited intonations of Yellow Group 4G and Yellow-Green Group 146D.

*Sepals.*—Size: Average 35–45 mm long×10–12 mm wide. Shape: Sepals generally narrow. Sepal apex is generally cirrose. Strong foliaceous appendages on three of the five sepals. Base is flat at union with receptacle. Quantity: Five. Surface texture: Inner side: Moderately pubescent. Outer surface: Nearly smooth. Stipitate glands are present. Color: Upper surface: Green Group 139D. Lower surface Green Group 139C. Intonations Greyed-Purple Group 163D, mostly on distal ends and margins.

Receptacle:

*Surface.*—Smooth, with limited numbers of fine, white hairs.

*Color.*—Red-Purple Group 183D.

*Shape.*—Funnel shaped.

*Size.*—8 mm (h)×12 mm (w).

Peduncle:

*Surface.*—With limited numbers of fine hairs and abundant stipitate glands.

*Length.*—40 mm average length.

*Diameter.*—4 mm average diameter.

*Color.*—Green Group 138A. Intonations of Red-Purple Group 183D.

*Strength.*—Thick, strong.

*Borne.*—Singly.

Flower bloom:

*Fragrance.*—Moderate floral scent.

*Duration.*—On the plant 10–15 days. Long lasting. As a cut flower, 8 to 10 days, with the flowers opening completely. Senesced petals drop away cleanly.

*Size.*—Large flowered garden rose. Average flower diameter is 80–100 mm when open.

*Form.*—Shape of flower when viewed from the side: Upon opening, upper part: Convex. Upon opening, lower part: Convex. Open flower, upper part: Convex. Open flower, lower part: Flattened convex.

Color:

*Upon opening, petals.*—Outermost petals: Outer Side: Red Group 52B. Inner Side: Red Group 55C. Innermost petals: Basal zone transitions to Yellow Group 11C. Outer Side: Red Group 39C. Inner Side: Red Group 39C.

*Upon opening, basal petal spots.*—Basal petal spot, outermost petals: Outer Side : Yellow Group 6C. Inner Side: Yellow Group 6C. Basal petal spot, innermost petals: Outer Side: Yellow Group 6C. Inner Side: Yellow Group 6C.

*After opening, petals.*—Outermost petals: Outer Side: Red Group 55D. Inner Side: Red Group 55C. Innermost petals: Outer Side: Red Group 38D. Inner Side: Red Group 38D.

*After opening, basal petal spots.*—Basal petal spot, outermost petals: Outer Side: Yellow Group 10D. Inner Side: Yellow Group 10C. Basal petal spot, innermost petals: Outer Side: Yellow Group 12D. Inner Side: Yellow Group 12C. Variegations: None.

General tonality: On open flower Red Group 39D. No change in the general tonality at the end of the $6^{th}$ day. Afterwards, general tonality is Red Group 49D.

Petals:

*Petal count.*—Very double. Approximately 70–80 petals under normal conditions.

*Petal reflex.*—Innermost petals reflex somewhat. Increasing on outermost petals, with outermost petals double reflexed, giving these petals a pointed shape.

*Petal edge.*—Entire, with limited undulations.

*Petal shape.*—Apex shape is round. Shape of base is deltoid.

*Petal size.*—50–60 mm long; 35–55 mm wide, with innermost petals being 35–40 mm wide.

*Thickness.*—Thick.

*Petal arrangement.*—Not formal.

*Petaloids.*—Present. Average of 4–6 per flower. Petaloids average 20 mm long and 15 mm wide. Color of inner side is Red Group 39C. Color of outer side is 39C. Not smooth. Shape is variable, from narrow to oval. Base is generally acute.

Reproductive organs:

*Pistils.*—Approximately 35–40 present. Interspersed with thicker stalks colored Green-White Group 157A. These stalks appear to be sterile pistils. Stigmas: Location: Superior in position to anthers. Color: Green-White Group 157A. Styles: Length: 12–15 mm long. Color: Green-White Group 157A. Intonations of Red-Purple Group 183C.

*Stamens.*—Approximately 50–60 on average, and regularly arranged. Anthers: Size: 2.5–3.0 mm long. Color: Grey-Brown Group 199C. Pollen: Generally present. Color: Greyed-Yellow Group 160B. Filaments: Color: Yellow Group 5B. Length: 10–12 mm.

THE PLANT

*Plant growth*.—Moderate vigor. Floriferous. Upright habit. When grown as a budded nursery plant, the average plant height is 120 cm and the average plant width is 60–70 cm.

*Stems*.—Stem color: Young wood: Green Group 138B. Juvenile stems with intonations of Greyed-Purple Group 183C. Older wood: Green Group 138B. Stem surface: Young wood: Smooth. Older wood: Smooth.

*Prickles*.—Present. Incidence: Flowering stems nearly thornless. Limited thorns present on the lower one half of the plant. On lower half of the plant, 2–3 thorns per 10 cm of stem. Size: Average length: 6 mm. Color: Immature prickles: Variable. Mostly Green Group 140D with intonations of Greyed-Purple Group 183C. Mature prickles: Grey-Brown Group 199D. Senescing to Greyed-Orange Group 167D. Shape: Deeply concave.

*Leaves and leaflets*.—Normally 5 leaflets on normal leaves in middle of the stem. Leaf size: 135–145 mm (l)×115–125 mm (w). Quantity: Average abundance. Texture: Upper surface glossy. Lower surface matte. Leathery. Color, mature foliage: Upper Leaf Surface: Green Group 137A. Lower Leaf Surface: Green Group 138A. Color, juvenile foliage: Upper Leaf Surface: Green Group 137A with intonations of Greyed-Purple Group 183C. Lower Leaf Surface: Green Group 138A. Anthocyanin intonation: Present. Location: Intonations present on juvenile leaflet margins, developing leaves, petioles, rachis, and stipules.

*Stipules*.—Size: 15–25 mm (l)×8–10 mm (w). Stipule color: Above: Green Group 138C. Below: Green Group 138C. Shape: Winged. Presence of stipitate glands: Abundant on margins. Margins: Serrated.

*Petiole*.—Smooth underneath. Length: 30–35 mm. Diameter: Average: 2.0 mm. Petiole color: Green Group 138B. Anthocyanin present on juvenile tissue, colored Greyed-Purple Group 183C. Prickles: Lacking. Stipitate glands: Moderate numbers of stipitate glands on upper margins.

*Petiole rachis*.—Length: 30–35 mm. Diameter: Average: 2.0 mm. Petiole color: Green Group 138B. Anthocyanin present on juvenile tissue, colored Greyed-Purple Group 183C. Prickles: Lacking. Stipitate glands: Moderate numbers of stipitate glands on margins. Stipitate glands are colored Greyed-Purple Group 183C.

*Leaflets*.—Size: Average size of the terminal leaflet in the mid portion of the plant is 60–65 mm (l) ×45 mm (w). Leaflet shape: Base: Rounded to obtuse. Apex: Rounded, coming to a slight point in the center. Margins: Finely serrated. Texture: Thick and leathery.

Hips/seed formation: None observed.

Winter hardiness: To date, the variety has been grown successfully in Zone 6.

Disease resistance: Above average resistance to powdery mildew and rust diseases under normal growing conditions.

I claim:

1. A new and distinct variety of rose plant characterized by the following combination of characteristics:

(a) forms attractive, long lasting pink flowers;

(b) exhibits an upright growth habit;

(c) propagates well using traditional methods, and;

(d) exhibits very good resistance to disease under normal growing conditions;

substantially as herein illustrated and described.

* * * * *

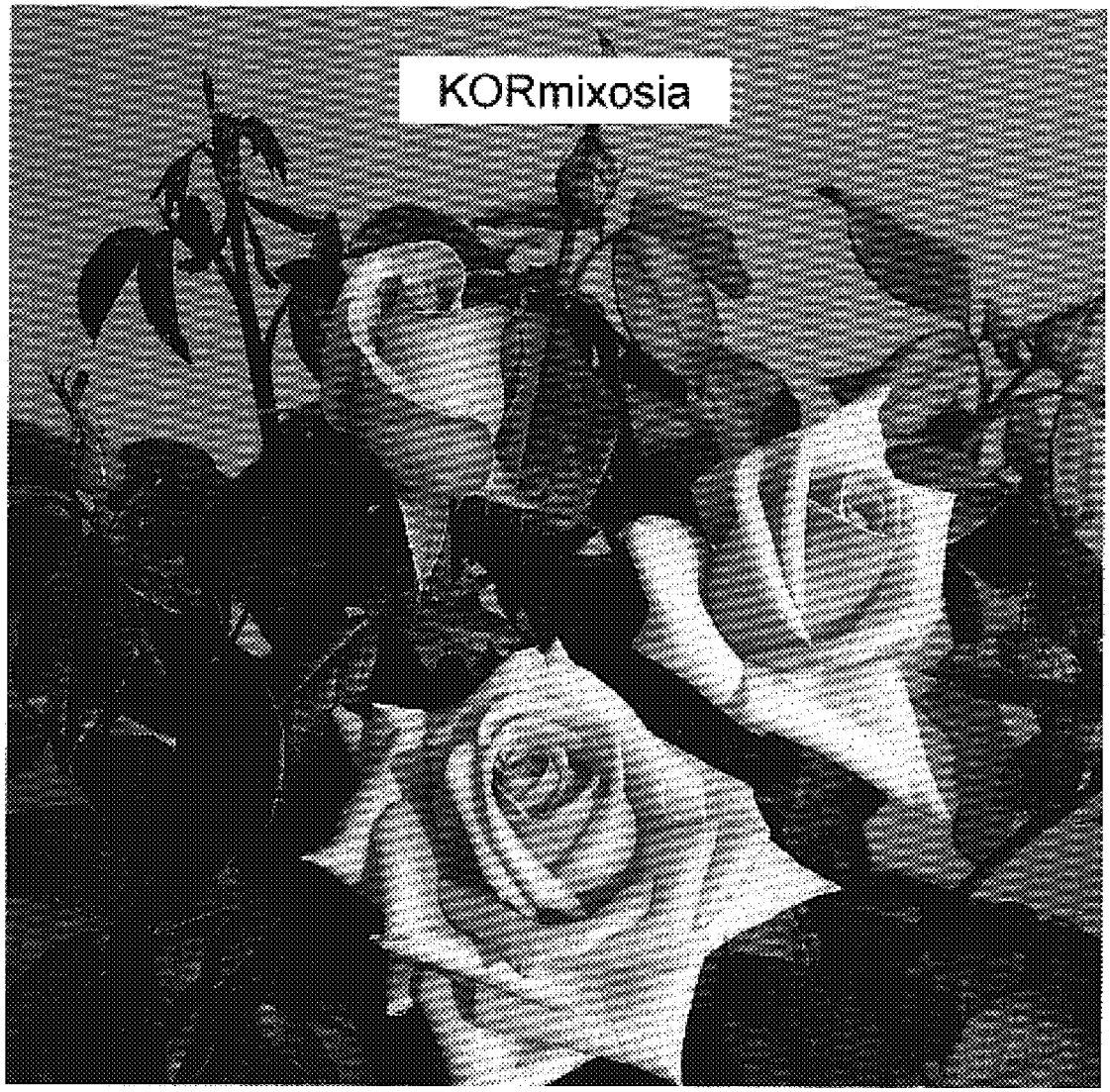
KORmixosia